United States Patent
McKnight

(10) Patent No.: US 9,523,132 B2
(45) Date of Patent: Dec. 20, 2016

(54) RAPID AND HIGHLY FIELDABLE VIRAL DIAGNOSTIC

(71) Applicant: UT-Battelle, LLC, Oak Ridge, TN (US)

(72) Inventor: Timothy E. McKnight, Greenback, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 14/212,718

(22) Filed: Mar. 14, 2014

(65) Prior Publication Data

US 2014/0272943 A1    Sep. 18, 2014

Related U.S. Application Data

(60) Provisional application No. 61/791,923, filed on Mar. 15, 2013.

(51) Int. Cl.
    *C12Q 1/70*    (2006.01)
(52) U.S. Cl.
    CPC ..................................... *C12Q 1/701* (2013.01)
(58) Field of Classification Search
    None
    See application file for complete search history.

(56) References Cited

U.S. PATENT DOCUMENTS

| 4,923,620 | A | 5/1990 | Pall |
| 4,925,572 | A | 5/1990 | Pall |
| 8,076,124 | B2 | 12/2011 | McKnight et al. |
| 2004/0197909 | A1 | 10/2004 | McKnight et al. |
| 2008/0171386 | A1 | 7/2008 | McKnight et al. |
| 2009/0087899 | A1 | 4/2009 | McKnight et al. |

FOREIGN PATENT DOCUMENTS

EP    0 313 348 A2    4/1989

OTHER PUBLICATIONS

Rosi and Mirkin (Chemistry Reviews, 2005, vol. 105, p. 1547-1562).*
McKnight, T.E., et al., "Synthetic nanoscale elements for delivery of materials into viable cells", Methods in Molecular Biology, 2005, pp. 191-208, vol. 303.
McKnight, T.E., et al., "Tracking Gene Expression after DNA Delivery Using Spatially Indexed Nanofiber Arrays", Nano Letters, 2004, pp. 1213-1219, vol. 4, No. 7.
Mann, D.G.J., et al., "Inducible RNA Interference-Mediated Gene Silencing Using Nanostructured Gene Delivery Arrays", ACS Nano, 2008, pp. 69-76, vol. 2, No. 1.
Gebhard, Lg., et al., " Functional RNA Elements in the Dengue Virus Genome", Viruses, 2011, pp. 1739-1756, vol. 3.
Leardkamolkarn, V., et al., "Establishment of a Stable Cell Line Coexpressing Dengue Virus-2 and Green Fluorescent Protein for Screening of Antiviral Compounds", Journal of Biomolecular Screening, 2012, pp. 283-292, vol. 17, published online Nov. 7, 2011.
Leardkamolkarn, V., et al., "Development of Dengue type-2 virus replicons expressing GFP reporter gene in study of viral RNA replication", Virus Research, 2012, pp. 552-562, vol. 163.
Manzano, M., et al. "Identification of cis-acting elements in the 3'-untranslated region of the dengue virus type 2 RNA that modulate translation and replication", J. Bio. Chem., 2011, vol. 286, No. 25, pp. 22521-22534.
Alcaraz-Estrada, S.L., et al., "Insights into dengue virus genome replication", Future Virol., 2010, pp. 575-592, vol. 5, No. 5.
Khromykh, A.A., et al., "cis- and trans-Acting Elements in Flavivirus RNA Replication", J. Virol., Apr. 2000, pp. 3253-3263, vol. 74, No. 7.
Woerz, I., et al., "Hepatitis C virus replicons: dinosaurs still in business?", J. Viral Hepatitis, 2009, pp. 1-9, vol. 16.
Tiley, L., et al., "The Foot-and-Mouth Disease Virus cis-Acting Replication Element (cre) Can Be Complemented in trans within Infected Cells", J. Virol., Feb. 2003, pp. 2243-2246, vol. 77, No. 3.
Steil, B., et al., "Cis-Active RNA Elements (CREs) and Picornavirus RNA Replication", Virus Res., Feb. 2009, pp. 240-252, vol. 139, No. 2.
Ljungberg, K., et al., "Increased Immunogenicity of a DNA-Launched Venezuelan Equine Encephalitis Virus-Based Replicon DNA Vaccine", J. Virol., Dec. 2007, pp. 13412-13423, vol. 81, No. 24, published online Oct. 3, 2007.
Tzeng, W., et al.,"Novel Replicon-Based Reporter Gene Assay for Detection of Rubella Virus in Clinical Specimens", J. Clin. Microbiol., Feb. 2005, pp. 879-885, vol. 43, No. 2.
Ge, F., et al., "High-throughput assay using a GFP-expressing replicon for SARS-CoV drug discovery", Antiviral Research, 2008, pp. 107-113, vol. 80.
Blight, K. J. and Nogard, E.A., "HCV Replicon Systems", Hepatitis C Viru: Genomes and Molecular Biology, Tan, SL, editor, Horizon Bioscience 2006, Chapter 11, pp. 311-351.

(Continued)

*Primary Examiner* — Agnieszka Boesen
(74) *Attorney, Agent, or Firm* — Scully Scott Murphy & Presser

(57) ABSTRACT

The present invention relates to a rapid, highly fieldable, nearly reagentless diagnostic to identify active RNA viral replication in a live, infected cells, and more particularly in leukocytes and tissue samples (including biopsies and nasal swabs) using an array of a plurality of vertically-aligned nanostructures that impale the cells and introduce a DNA reporter construct that is expressed and amplified in the presence of active viral replication.

24 Claims, No Drawings

(56) References Cited

OTHER PUBLICATIONS

Nivens, D.E., et al., "Bioluminescent bioreporter integrated circuits: potentially small, rugged and inexpensive whole-cell biosensors for remote environmental monitoring", J. App. Microbiol., 2004, pp. 33-46, vol. 96.
Chan, Y. K., et al.: "IFITM Proteins Restrict Antibody-Dependent Enhancement of Dengue Virus Infection", PLoS One, Mar. 2012, e34508, vol. 7, issue. 3, doi:10.1371/journal.pone.0034508.
Dominguez, C., et al., "HADDOCK: a protein-protein docking approach based on biochemical or biophysical information", J. Am. Chem. Soc., 2003, pp. 1731-1737, vol. 125.
Shapiro, B.A., et al., "RNA folding pathway functional intermediates: Their prediction and analysis", J. Mol. Biol., 2001, pp. 27-44, vol. 312.
Sharma, S., et al., "iFoldRNA: Three-dimensional RNA structure prediction and folding", Bioinformatics, 2008, pp. 1951-1952, vol. 24, No. 17.
Ansarah-Sobrinho, C., et al., "Temperature-dependent production of pseudoinfectious dengue reporter virus particles by complementation", Virology, 2008, pp. 67-74, vol. 381.
Arzt, J., et al., "The Early Pathogenesis of Foot-and-Mouth Disease in Cattle After Aerosol Inoculation: Identification of the Nasopharynx as the Primary Site of Infection", Veterinary Pathology, Infectious Disease, published online Jun. 29, 2010, pp. 1048-1063, vol. 47, No. 6.
Charleston, B., et al., "Relationship Between Clinical Signs and Transmission of an Infectious Disease and the Implications for Control", Science, May 6, 2011, pp. 726-729, vol. 332.
Zhang, J., et al. "Helper virus-independent trans-replication of hepatitis C virus-derived minigenome", Biochemical and Biophysical Research Communications, 2007, pp. 170-176, vol. 352.
Alcaraz-Estrada, S.L., et al., "Supplementary Methods (5 pages)—Construction of a dengue virus type 4 reporter replicon and analysis of temperature-sensitive mutations non-structural proteins 3 and 5", J. Gen. Virol., Nov. 2010, pp. 2713-2718, vol. 91, printed online Jun. 29, 2010.
Close, D.M., et al., "In Vivo Bioluminescent Imaging (BLI):Noninvasive Visualization and Interrogation of Biological Processes in Living Animals", Sensors, 2011, pp. 180-206, vol. 11.
Alcaraz-Estrada, S.L., et al., "Construction of a dengue virus type 4 reporter replicon and analysis of temperature-sensitive mutations in non-structural proteins 3 and 5", Journal of General Virology, 2010, pp. 2713-2718, vol. 91.
Paranjape, S. M., et al., "Control of Dengue Virus Translation and Replication", Science and Technology Policy Fellowship Program, American Association for the Advancement of Sciences,1200 New York Avenue NW, Washington DC, USA 20005, e-mail: sumip1@gmail.com, pp. 15-34.
Schaller, T. et al., "Analysis of Hepatitis C Virus Superinfection Exclusion by Using Novel Fluorochrome Gene-Tagged Viral Genomes" Journal of Virology, 81(9):4591-4603, 7327 (2007).
Zou, G. et al. "Exclusion of West Nile Virus Superinfection through RNA Replication" Journal of Virology 83 (22):11765-11776 (2009).

* cited by examiner

RAPID AND HIGHLY FIELDABLE VIRAL DIAGNOSTIC

This application claims priority from U.S. Provisional Patent Application No. 61/791,923, filed on Mar. 15, 2013, entitled "Rapid and Highly Fieldable Viral Diagnostic", the entire contents of which are incorporated herein by reference.

This invention was made with government support under Prime Contract No. DE-AC05-00OR22725 awarded by the U.S. Department of Energy. The government has certain rights in the invention.

FIELD OF THE INVENTION

The present invention relates to a rapid, highly fieldable, nearly reagentless diagnostic to identify active RNA viral replication in live, infected cells, and more particularly in samples comprising blood, tissue biopsies, isolated cells, intact tissue, or regions of tissue in situ (e.g., at a viral lesion or site of infection) using an array of a plurality of vertically aligned high aspect ratio nanostructures that introduce at least one DNA reporter construct into the nuclei of cells within the sample, by inserting or impaling the sample onto the array of a plurality of vertically aligned nanostructures. In one particular embodiment, the at least one DNA reporter construct contains a single or plurality of genes encoding a reporter gene and nucleotide sequences specific for a particular virus, and is transcribed by impaled cells to mRNA, however, the mRNA is virally-replicated only in impaled cells that are infected with the virus that the at least one DNA reporter construct contains nucleotide sequences specific for that particular virus. The signal from the reporter gene encoded by the at least one DNA reporter construct is indicative of active viral replication and infection by the specific RNA virus.

BACKGROUND OF THE INVENTION

RNA viruses represent a significant portion of the high priority pathogens of concern to both human and animal health. The National Institute of Allergy and Infection Diseases' (NIAID) prioritized listing of human pathogens includes the RNA viruses: Hanta viruses, Dengue, Ebola, Marburg, Lassa, Hepatitis A and C, West Nile, and a large number of encephalitis viruses. The USDA prioritized list of infectious animal diseases include four RNA viruses within their top six ranked pathogens: Foot and Mouth Disease Virus, Rift Valley Fever Virus, common swine fever virus, and Japanese encephalitis virus. Viral outbreaks of these pathogens have significant direct impact on human health or dramatic indirect impact by their disruption of food supplies and related economic considerations. Hence, a rapid diagnostic would be an important and effective response to viral outbreaks. However, the current diagnostics are limited by both available technology and implementation.

For example, Dengue virus is a mosquito-borne viral pathogen prioritized by the World Health Organization (WHO) as it endangers 40% of the world's population, or 2.5 billion people, with over 50-100 million new infections each year. The WHO's 'Gold Standard' assays for Dengue include the plaque reduction neutralization assay, the haemmagglutination inhibition assay, and an IgM capture ELISA, and each of these methods require significant clinical infrastructure as well as both acute and convalescent samples from the patient for result validation. Current so-called "rapid" diagnostic tests have emerged based upon serology (IgM and IgG based methods), viral genetics (RT PCR methods), and viral isolation (cell culture and mosquito inoculation). However, these approaches are limited by costs, accuracy and sensitivity, and temporal considerations. Low-cost diagnosis of early onset Dengue is simply not practical, especially in remote settings where Dengue is rampant and clinical infrastructure is unavailable.

In the animal virus field, foot and mouth disease (FMD) is the most contagious transboundary animal disease affecting bovids and other cloven-hoofed animals. Significant economic losses result from its high morbidity, and from tourism and export trade restrictions imposed on affected countries. While the U.S. has not had a case of FMD since 1929, the country remains vigilant against its import and potential bioterrorism to protect against the devastating economic impacts of this disease. FMD is caused by infection of a picornavirus, a non-enveloped, positive-strand RNA virus. Previremic infection is often localized to epithelial tissues of the nasopharynx, due to aerosolized airborne contamination [Artz, 2010]. Active viral replication occurs during a preclinical phase of infection within this tissue and then continues in the lungs and endovascularly during the viremia phase. Viral replication is via an RNA-dependent RNA polymerase, D3pol, encoded by the virus whereby the RNA genome of the virus is replicated and packaged within the cytoplasm of infected cells.

Current methodologies for assay of FMD rely on detection of viral antigens and/or viral RNA, and do not require these markers to be active nor intact. Both approaches typically require laboratory clinical analyses. While fieldable kits are becoming available for ELISA-based detection, they have low sensitivity, and, importantly, do not provide an indication of active/transmissible infection. Charleston et al. (Science 2011) indicate that the infectious period of FMD is much shorter than previously realized (mean 1.7 days) and animals are not infectious until approximately 0.5 days after the onset of clinical symptoms. As such, costly remediation measures of herd culling may be unnecessary if accurate, fieldable methods for determination of infectiousness can be achieved.

The present invention overcomes the shortcomings of these assays and provides a highly fieldable, rapid diagnostic system for pathogenic RNA viruses

SUMMARY OF THE INVENTION

The present invention is directed to a method of using an array of a plurality of vertically aligned high aspect ratio nanostructures that are incorporated with, via either coating or covalent attachment, DNA encoding at least one reporter construct. The DNA-incorporated array of a plurality of vertically aligned high aspect ratio nanostructures is capable of introducing the DNA into a sample, such as, blood, tissue biopsies, isolated cells, intact tissue, or regions of tissue in situ (e.g., at a viral lesion or site of infection), wherein the DNA incorporated on the array of a plurality of vertically aligned high aspect ratio nanostructures is delivered to the nulcei of cells within the sample, where it is transcribed into mRNA. In one embodiment, the mRNA, transcribed from the at least one reporter DNA construct is a viral reporter replicon capable of producing a detectable signal, such as a fluorescence, luminescence, or an antigen, and is capable of being recognized and replicated by a replicase and/or RNA polymerase that is specific to the virus to be detected. The reporter replicon is a subgenomic fragment of the specific virus to be detected, comprising an RNA message for a reporter protein which is flanked by the 5' and 3' untranslated regions (UTRs) of the target virus and may include other genetic sequences from the target virus up to and including the whole genome, but typically with at least the viral replicase gene deleted or disabled such that replication of the replicon can only occur in already virally infected cells, or with the replicase gene remaining intact thereby providing a positive control assay whereby the replicon is amplified even in non-infected cells. The combined use of UTR-flanked replicon reporters and high aspect ratio nanostructure-mediated gene delivery platform thereby enables a near reagentless assay for specific viral infections directly within suspect viral lesions, infected tissues, or isolated cells. The technique is rapid, specific and sensitive due to immediate transgene expression and subsequent viral amplification of the mRNA. The technique is sensitive to early acute infection, and the technique advantageous over existing methods due to significantly less requirements for clinical infrastructure.

DETAILED DESCRIPTION OF THE INVENTION

The present invention is directed to a highly fieldable method for rapid diagnosis of RNA viral infections in samples, such as, for example, blood, biological fluid, tissue biopsies, isolated cells (such as, for example, peripheral blood mononucleated cells), intact tissue, or regions of tissue in situ (e.g., at a viral lesion or site of infection). In one embodiment, the method does not need significant infrastructure, is nearly reagentless and can be configured to avoid the need for cold storage when implemented for the field.

In one embodiment, the present invention provides a method which is performed by (a) adsorbing either (i) a peripheral blood sample onto a porous filter to entrap leukocytes but permit gravimetric flow through of platelets and red blood cells, (ii) a tissue sample onto a filter or other surface material, (iii) a body fluid sample or (iv) a sample of leukocytes onto a filter or other surface; (b) impaling the sample on the filter or surface material onto an array of a plurality of vertically aligned high aspect ratio nanostructures capable of penetrating the plasma membrane and the nucleus of cells within the sample, wherein the high aspect ratio nanostructures are incorporated with at least one DNA reporter construct, wherein the at least one DNA reporter construct encodes a viral replicon comprising an mRNA sequence containing cis-acting RNA viral replication elements for a specific virus, that flank and are operably linked to RNA sequence encoding a reporter protein, and which cis-acting RNA viral replication elements are capable of complementation in trans with viral replication factors in virally-infected cells to thereby replicate and amplify the entire reporter construct; and (c) detecting the characteristics of the expressed reporter such as rate of gain of the signal from the reporter protein, corresponding to the presence of cells with active viral replication and infection.

A plurality of non aligned nanostructures may also be employed to introduce the at least one DNA reporter construct into cells. For example, the at least one DNA reporter construct may be introduced into the sample using a plurality of silicon carbide whiskers. Alternatively, the at least one DNA reporter construct may be introduced into the sample via bombardment of the sample with DNA-loaded microprojectiles.

Detection of the expressed reporter may be by any convenient means, such as, for example fluorescence and luminescence. In one embodiment, the method of the present invention is configured to allow detection of the reporter by a portable, and/or handheld instrument.

In one embodiment, once the sample is impaled onto the array of a plurality of vertically aligned high aspect ratio nanostructures, no further reagents are needed to drive reporter expression because the sample provides the transcriptional machinery necessary for production of the UTR-flanked reporter mRNA. In actively virally infected cells, the presence of viral replication factors serve to amplify the reporter mRNA which is then translated from higher copy numbers of mRNA for reporter expression. The direct development of the reporter signal is then detected, and since it can be a fluorescence signal or a bioluminescence signal, only a detector is needed (and an excitation source to generate fluorescence, which is generally part of the detector system).

Sample Preparation:

In one embodiment, the method of the present invention is implemented by obtaining a small sample of blood, for example, from a finger prick, applying a droplet of that blood to a filter, optionally washing the filter with a small amount of buffer, pressing the filter against a plurality of vertically aligned high aspect ratio nanostructures coated with a least one DNA reporter construct specific for the RNA virus to be detected and then detecting expression of the reporter.

The blood sample may originate from humans or, alternatively animals. Blood samples may be obtained by blood collection methods which are well known in the art. For example, individuals can be subjected to a finger prick or can have venous blood withdrawn. Animals can also have venous blood withdrawn or be cut, nicked or pricked at an easily accessible site such as an ear. For example, rabbit and cattle ears can be nicked to obtain blood, and venous blood can be withdrawn from rodent tails or the tails and jugular veins of cattle. In one embodiment, the volume of the blood sample needed is minimal, such that a single, small droplet (ranging from as little as 10-50 µl to 100-400 µl) is all that is necessary. Such small amounts can be obtained from a finger prick.

In an alternate embodiment, the method of the present invention is implemented by obtaining a small sample of body fluid, such as, for example, a lung lavage, nasal mucus, and the like, applying a droplet of that sample to a filter, optionally washing the filter with a small amount of buffer, pressing the filter against a plurality of vertically aligned high aspect ratio nanostructures coated with a least one DNA reporter construct specific for the RNA virus to be detected and then detecting expression of the reporter.

The sample may be transferred onto the porous filter by any suitable method. For example, the sample may be touched directly to the porous filter. Alternatively, the sample may be first drawn into a small capillary tube which in turn is touched to the filter. Alternatively, the apparatus used to obtain the sample may be touched to the filter (thereby allowing a small amount of sample to "wick" onto the filter). Alternatively, a drop of sample may be pipetted on to the porous filter.

In an alternative embodiment, the sample is a tissue sample, which as used herein includes tissue biopsies, nasal swabs, or intact tissue in situ. Tissue biopsies are obtained from suspected viral lesions, or other tissues known as sites for viral replication, by methods well known in the art. For example, needle biopsies can be used to obtain cellular material from a viral lesion.

In one embodiment, once a sample is adsorbed on the filter, the filter is used immediately. In an alternate embodiment, the filter may be stored for assay at a later time. In an alternate embodiment, the sample is stored for later assay, once the sample is collected. Sample storage may include freezing, provided significant cell viability is retained to perform the assay.

In certain embodiments, such as, for example, when the method of the present invention is employed in the field, or where minimal medical facilities are available, sample collection and transfer to the filter should be done with a minimum of infrastructure and with clean or sterile technique to the extent possible.

In one embodiment, the sample is treated prior to absorption onto the porous membrane. In one embodiment, the sample is treated to enrich the sample for a certain cell type. In one embodiment, the sample is treated to increase the transcription of the at least one reporter construct. In one embodiment, the sample is treated to increase the translation of the at least one reporter construct. In one embodiment, the sample is treated to increase both the transcription and translation of the at least one reporter construct.

In one embodiment, the sample is blood, and the blood is treated to enrich the leukocytes within the blood sample. Enrichment may be achieved by any suitable method readily selected by one of skill in the art, such as, for example, centrifugation, density gradient centrifugation, or buffy coat or buffy layer methods.

Other enrichment methods may include filtration, affinity purification and the like. In an alternate embodiment, the porous filter enriched the sample. For example, in one embodiment, the porous filter retains cells, however, liquids such as buffers, and cellular debris are not retained and pass through the filter. In one embodiment where the present invention is employed to detect viral infection in samples obtained from tissue biopsies, the porous filter has sufficient porosity to retain cells while allowing flow through of buffer or cellular debris.

In one embodiment, the tissue biopsy material is smeared directly onto a porous filter and, optionally, washed with a small volume of buffer. In one embodiment, the filter is non porous.

In one embodiment, the porous filter is treated with an agent that enriches the sample for a specific cell type. Enrichment may be achieved by any suitable method readily selected by one of skill in the art, such as, for example, affinity purification.

The porous filters may be washed, if needed, with any physiological buffer solution that maintains cell viability at an acceptable level. An acceptable level of viability means that at least about 30-50% or more of the cells are viable.

Porous filters for processing samples comprise a fibrous adsorption-filtration filter medium capable of retaining cells from a sample. The number of cells retained by the porous filter should be sufficient to detect the presence of infected cells within the sample. For example, in an embodiment utilizing a blood sample, a porous filter retains from at least about 30 to about 80% of the applied leukocytes after washing to remove the red blood cells (RBCs).

Typically, a small blood sample of a set volume is adsorbed or deposited upon a porous filter and then washed with 2-3 volumes of buffer. A particularly useful filter, for example, has a nominal pore size of about 8 microns and is capable of 40-80% leukocyte immobilization with a 70-80% post-wash leukocyte retention rate. The filters are extremely hydrophilic and wettable with solutions having surface tensions of up to 85-90 dynes with a hold up volume of 40-70 µl/cm$^2$ for a single layer of adsorption-filtration filter medium and low to medium protein binding. Example of such filters, include but are not limited to, LEUKOSORB TYPES A and B (trademark Pall Corp.) and those described in U.S. Pat. Nos. 4,923,620, 4,925,572, or European Patent No. 313348.

In the method of the present invention, after the sample has been absorbed onto the porous membrane, the sample is then impaled onto the array of a plurality of high aspect ratio nanostructures. As used herein the term "impalefection" refers to the transfection of cells by physical impalement via a plurality of vertically aligned high aspect ratio nanostructures.

In one embodiment, the sample is impaled onto the array of a plurality of vertically aligned high aspect ratio nanostructures by any one of the methods disclosed in McKnight et al, Methods in Molecular Biology, vol 303: NanoBiotechnology Protocols, 2005, pp 191-208.

In one embodiment, the sample is impaled onto the array of a plurality of vertically aligned high aspect ratio nanostructures by any one of the methods disclosed in McKnight et al, Nano Letters, vol 4, 2004, p 1213-1219.

In one embodiment, the sample is impaled onto the array of a plurality of vertically aligned high aspect ratio nanostructures by any one of the methods disclosed in U.S. Patent Application 2004/0197909 A1.

In one embodiment, the sample is impaled onto the array of a plurality of vertically aligned high aspect ratio nanostructures by any one of the methods disclosed in U.S. Patent Application 2008/0171386 A1.

In one embodiment, the sample comprises cells, and the sample is impaled onto the array of a plurality of vertically aligned high aspect ratio nanostructures via forming a cell pellet, and subsequently pressing the array of a plurality of vertically aligned high aspect ratio nanostructures against the pellet.

In one embodiment, the sample is impaled onto the array of a plurality of vertically aligned high aspect ratio nanostructures via first absorbing the sample onto a porous membrane, and subsequently pressing the array of a plurality of vertically aligned high aspect ratio nanostructures against the membrane.

In one embodiment, the sample is impaled onto the array of a plurality of vertically aligned high aspect ratio nanostructures the impalefection system described in Mann et al. (2008) ACS Nano 2: 69-76.

In one embodiment, the sample consists of peripheral blood mononucleated cells. In one embodiment, the peripheral blood mononucleated cells are purified from whole blood obtained from a finger prick, or other blood sample collection method. In one embodiment, the blood sample is applied to a porous filter, such as, for example, the hydrophilic Leukosorb filter, wherein the blood mononucleated cells are trapped and the remaining, unwanted elements in the whole blood sample are rinsed away. The sample now trapped on the porous filter is then impaled onto the array of a plurality of vertically aligned nanostructures by pressing the porous filter onto the array.

High Aspect Ratio Nanostructures: The present invention employs an array of a plurality of vertically aligned high aspect ratio nanostructures capable of penetrating the cell membrane of cells within the sample. In certain embodiments, the plurality of vertically aligned high aspect ratio nanostructures are capable of penetrating the cell membrane and nuclear membrane of cells within the sample.

Nanostructures suitable for use in the present invention are dimensioned such that a nanostructure may be inserted into the intracellular domain of many cell types. The nanostructures are capable of being synthesized with an exceptional degree of control, tailoring the physical properties of size, location on a substrate, and chemical composition. For example, by way of illustration, using a plasma-enhanced chemical vapor deposition (PECVD) process, allows carbon nanofibers to be synthesized at specific locations upon a substrate as defined by the lithographic patterning of catalyst metals, such as Ni, Co, and Fe.

In one embodiment, nanostructures are formed by a first step, wherein catalyst material is nucleated from a thin film on the substrate into nanoscale droplets. During subsequent fiber growth, each catalyst droplet precipitates the deposition of carbon from the gas phase, forming a carbon fiber. Based upon growth parameters, the resultant structure may be a chaotic winding of carbonaceous material (base-growth) or may result in highly aligned, vertically-oriented fibers that grow perpendicular to the substrate (tip-growth). The mechanisms of tip-growth provide a high degree of control over the ultimate shape of vertically-aligned nanostructures, including ultimate fiber length, tip diameter, and geometry (conicity). Typically, nanostructures may be grown several microns in length, with tip diameters as small as tens of nanometers. In addition to geometry, surface chemistry (and surface charge) may also be tailored by adjusting the ratio of the carbonaceous source gas and an etchant gas, which is introduced to the plasma process during fiber growth.

The high aspect ratio of nanostructures, their small nanoscale tips, and the ability to synthesize these nanoscale elements at defined locations, enable them to be implemented in systems that integrate with whole cells and cellular matrices. Further, the ability to synthesize vertically-aligned nanostructures in parallel arrays, provides basis for integrating many fibers with cells in a parallel manner.

Nanostructures of suitable for use in the present invention include a construct featuring numerous types of functional groups that may be modified by organic chemistry reactions. Nanostructures of suitable for use in the present invention feature rich surface chemistries (carboxy, carboxylic acid, hydroxy, quinone, amine groups, for example), a variety of derivitization chemistries may be employed to modify the surface of the nanostructure with large and small molecules. Additionally, the nanostructure may be physically coated with other materials, enabling other attachment chemistries. Physical coating may include, for example, PECVD oxide coating followed by MAPTOS/pNIPAM (poly n isopropyl acrylamide), or metallization via sputtering, physical vapor deposition, and electroplating, or electrochemical polymerization coating with parylene.

The array of a plurality of vertically aligned high aspect ratio nanostructures may be grown on any type of substrate (conductive, nonconductive, opaque, transparent) that can survive the PECVD growth process (700° C.). Typical substrates are silicon and quartz (fused silica).

In one embodiment, the present invention employs an array of a plurality of vertically aligned high aspect ratio nanostructures, with an average spacing between nanostructures of about 3 to about 20 microns. In one embodiment, the array of a plurality of vertically aligned high aspect ratio nanostructures are a plurality of nanotubes. In an alternate embodiment, the array of a plurality of vertically aligned high aspect ratio nanostructures are a plurality of nano-spikes.

In one embodiment, the array of a plurality of vertically aligned high aspect ratio nanostructures are made from carbon. In an alternate embodiment, the array of a plurality of vertically aligned high aspect ratio nanostructures are made from $SiO_2$. In an alternate embodiment, the array of a plurality of vertically aligned high aspect ratio nanostructures are made from a combination of carbon and $SiO_2$.

In one embodiment, the array of a plurality of vertically aligned high aspect ratio nanostructures are made from micro-machined silicon. In an alternate embodiment, the plurality of vertically aligned high aspect ratio nanostructures are made from zinc oxide. In an alternate embodiment, the plurality of vertically aligned high aspect ratio nanostructures are made from indium arsenide. In an alternate embodiment, the plurality of vertically aligned high aspect ratio nanostructures are made from silicon. In one embodiment, the silicon is black silicon.

In one embodiment, the array of a plurality of vertically aligned high aspect ratio nanostructures comprise a plurality of the vertically aligned high aspect ratio nanostructures disclosed in McKnight et al, Methods in Molecular Biology, vol 303: NanoBiotechnology Protocols, 2005, pp 191-208.

In one embodiment, the array of a plurality of vertically aligned high aspect ratio nanostructures are manufactured by any one of the methods disclosed in McKnight et al, Methods in Molecular Biology, vol 303: NanoBiotechnology Protocols, 2005, pp 191-208.

In one embodiment, the array of a plurality of vertically aligned high aspect ratio nanostructures comprise a plurality of the vertically aligned high aspect ratio nanostructures disclosed in McKnight et al, Nano Letters, vol 4, 2004, p 1213-1219.

In one embodiment, the array of a plurality of vertically aligned high aspect ratio nanostructures are manufactured by any one of the methods disclosed in McKnight et al, Nano Letters, vol 4, 2004, p 1213-1219.

In one embodiment, the array of a plurality of vertically aligned high aspect ratio nanostructures are the vertically aligned high aspect ratio nanostructures disclosed in U.S. Patent Application 2004/0197909 A1.

In one embodiment, the array of a plurality of vertically aligned high aspect ratio nanostructures are manufactured by any one of the methods disclosed in U.S. Patent Application 2004/0197909 A1.

In one embodiment, the array of a plurality of vertically aligned high aspect ratio nanostructures comprise a plurality of the vertically aligned high aspect ratio nanostructures disclosed in U.S. Patent Application 2008/0171386 A1.

In one embodiment, the array of a plurality of vertically aligned high aspect ratio nanostructures are manufactured by any one of the methods disclosed in U.S. Patent Application 2008/0171386 A1.

In one embodiment, the array of a plurality of vertically aligned high aspect ratio nanostructures comprise a plurality of the vertically aligned high aspect ratio nanostructures disclosed in U.S. Patent Application 2009/0087899 A1.

In one embodiment, the array of a plurality of vertically aligned high aspect ratio nanostructures are manufactured by any one of the methods disclosed in U.S. Patent Application 2009/0087899 A1.

In one embodiment, the length of an individual nanostructure within the array of a plurality of vertically aligned nanostructures is from about 3 microns to about 50 microns.

In one embodiment, the tip diameter of an individual nanostructure within the array of a plurality of vertically aligned nanostructures does not exceed 100 nm.

In an alternate embodiment, the array used to impalefect the sample is an array of a plurality of vertically aligned micro-machined needles, wherein the tip of each individual micro-machined needle is formed into an individual nanostructure, wherein the length of an individual nanostructure is from about 3 microns to about 50 microns, and the tip diameter of an individual nanostructure does not exceed 100 nm.

In an alternate embodiment, the array used to impalefect the sample is an array of a plurality of vertically aligned microneedles, wherein the tip of each individual microneedle is formed into an individual nanostructure, wherein the length of an individual nanostructure is from about 3 microns to about 50 microns, and the tip diameter of an individual nanostructure does not exceed 100 nm.

Incorporation of DNA onto the Array of a Plurality of Vertically Aligned High Aspect Ratio Nanostructures: In one embodiment, the array of a plurality of vertically aligned high aspect ratio nanostructures are coated with at least one DNA reporter construct to provide delivery of the at least one DNA reporter construct to a sample.

U.S. Patent Application 2009/0087899 A1 provides detailed information on one possible mechanism for the preparation and coating of the array of a plurality of vertically aligned high aspect ratio nanostructures as well as the arrangement of the array of a plurality of vertically aligned high aspect ratio nanostructures in arrays or other formats, and how to use the array of a plurality of vertically aligned high aspect ratio nanostructures to impale and transfect cells and various methods to detect the reporter signal. Typically, the at least one DNA reporter construct is dried onto the array of a plurality of vertically aligned high aspect ratio nanostructures and can be stored in a desiccated condition for long periods of time without substantial degradation. Other methods, such as covalent attachment of the DNA to the array of a plurality of vertically aligned high aspect ratio nanostructures are available, again providing the DNA in stable form without substantial degradation for long periods of time.

Methods for coating the array of a plurality of vertically aligned high aspect ratio nanostructures are described in U.S. Patent Application 2009/0087899 A1. Without limitation, the stably-coated array of a plurality of vertically aligned high aspect ratio nanostructures contribute one aspect of making the present invention a highly fieldable diagnostic assay for pathogenic RNA viruses.

In one embodiment, the at least one DNA reporter construct is dispensed directly onto the array of a plurality of vertically aligned high aspect ratio nanostructures in volume of liquid from about 1 µl to about 3 µl, and allowing the liquid to dry. The concentration of the at least one DNA reporter construct may be from about 1 ng/µl to about 1000 ng/µl.

In an alternate embodiment, the at least one DNA reporter construct is covalently attached to the array of a plurality of vertically aligned high aspect ratio nanostructures. Here, the at least one DNA reporter construct is dispensed directly onto the array of a plurality of vertically aligned high aspect ratio nanostructures in volume of liquid from about 1 µl to about 3 µl, and the at least one DNA reporter construct is subsequently covalently attached to the array of a plurality of vertically aligned high aspect ratio nanostructures. Covalent attachment may be achieved by any suitable method, such as, for example, the methods disclosed in McKnight et al, Nano Letters, vol 4, 2004, p 1213-1219. The concentration of the at least one DNA reporter construct may be from about 1 ng/µl to about 1000 ng/µl.

The at Least One DNA Reporter Construct: In one embodiment, the at least one DNA reporter construct comprises DNA sequences encoding viral-specific cis-acting replication elements operably linked to an RNA message of a reporter gene, genes or operon, and is transcribed in virally-infected and non-infected cells. However, and importantly, due to the presence of viral replicase activity the RNA can only be further amplified in virally-infected cells—not in non-infected cells. The at least one DNA reporter construct encodes an mRNA featuring a reporter operon or gene flanked by specific viral 3' and 5' untranslated regions (UTRs) and any adjacent regions necessary from the viral genome which serve as cis-acting elements for viral replication and amplification of the reporting mRNA signal. The mRNA launched from the at least one DNA reporter construct is therefore a viral replicon that requires provision of one or more of the trans-acting elements required for viral replication and/or transcription.

In certain embodiments, the at least one reporter construct is a DNA reporter construct encoding an mRNA featuring a reporter operon or gene flanked by specific viral 3' and 5' untranslated regions (UTRs) and regions adjacent to the UTRs which serve as cis-acting elements for viral replication and amplification of the reporting mRNA signal.

The cis- and trans-acting elements needed for viral replication and mRNA amplification vary by virus and are known in the art, as are specific requirements for construction of the flanked reporter construct to enable expression of the mRNA and replication by viral infection. The UTRs and any necessary adjacent regions can be constructed for negative or positive-stranded RNA virus. These may be launched from a constitutively expressed DNA construct whereby constitutively-expressable used herein means that the transcriptional promoter is constitutive, and thus always "on". One example of a constitutive promoter is the human cytomegalovirus immediate early promoter, CMVie. Many constitutive promoters are known to those of skill in the art.

Human pathogenic RNA viruses include, but are not limited to, Hanta viruses, Dengue, Ebola, Marburg, Lassa, Hepatitis A and C, West Nile, yellow fever, and a large number of encephalitis viruses. Animal pathogenic RNA viruses include, but are not limited to, Foot and Mouth Disease Virus, Rift Valley Fever Virus, common swine fever virus, and Japanese encephalitis. Viral replicons that work in trans with viral replication and transcription proteins are known in the art. Examples of viral replicons that are suitable for adaption into the reporter constructs of the invention are described for Dengue in Gebhard et al. (2011) Viruses 3:1739-1756; Leardkamolkarn et al (2012) J. Biomole. Screening 17:283-292; Leardkamolkarn et al (2012) Virus Res. 163: 552-562; Manzano et al (2022) J. Biol. Chem. 286:22521-22534: and Alcaraz-Estrada et al. (2010) Future Virol. 5: 575-592; Ansarah-Sobrinho C et al (2008) Virology 381: 67-74.

for a flavivirus (Kunjin, related to Japanese encephalitis virus) in Khromykh et al. (2000) J. Virol. 74:3253-3263 for Hepatitis C virus in Zhang et al. (2007) Biochm. Biophys. Res. Commun. 352:170-176; Woerz et al. (2009) J. Viral Hepatitis 16:1-9;

for Foot and Mouth Disease virus (FMDV) in Tiley et al. (2003) J. Virol. 77:2243-2246; and for Picorna viruses (which includes FMDV and others) in Steil et al. (2009) Virus Res. (2009) 139:240-252.

In one embodiment, the at least one DNA reporter construct launches an mRNA that contains a 5' nucleotide sequence that encodes a 5'UTR of the virus to be detected in addition to adjacent nucleotides in the coding region of the viral genome, linked to a nucleotide sequence that encodes a reporter protein, which is in turn linked to a nucleotide sequence that encodes the 3' UTR of the virus to be detected.

In one embodiment, the nucleotide sequence encoding the 5' UTR encodes sequences that enhance viral replication of the mRNA launched from the at least one DNA reporter construct, such as, for example, sequences involved in long-range RNA-RNA interaction, genome replication, or genome circularization. In one embodiment, the sequence encoding the 5' UTR is a sequence of 160 nucleotides.

In one embodiment, the nucleotide sequence encoding the 3' UTR encodes a sequence that enhances viral replication, such as, for example, sequences involved in long-range RNA-RNA interaction, genome replication, or genome circularization. In one embodiment, the sequence encoding the 3' UTR is a sequence of 450 nucleotides.

In one embodiment, a viral replicon suitable for adaption into an at least one DNA reporter construct of the present invention is the Serotype 2 of Dengue virus replicon (DenV sero2) disclosed in Leardkamolkarn et al (2012) Virus Res. 163: 552-562. In one embodiment, the reporter lacks the nucleotide sequence encoding the NS5 replicase, and therefore, only virally infected cells are capable of replicating the reporter construct.

In one embodiment, a DNA reporter construct that indicates active viral replication and infection by DenV sero2 is created using the methods described in Leardkamolkarn et al (2012) Virus Res. 163: 552-562.

In one embodiment, a viral replicon suitable for adaption into an at least one DNA reporter construct of the present invention is the Dengue virus replicon disclosed in Gebhard et al (2011) Viruses 3, 1739-1756.

In one embodiment, a DNA reporter construct that indicates active viral replication and infection by Dengue virus created using the methods described in Gebhard et al (2011) Viruses 3, 1739-1756.

In one embodiment, a viral replicon suitable for adaption into an at least one DNA reporter construct of the present invention is the Equine Encephalitis virus replicon (EEV) disclosed in Ljungberg et al (2007) J. Virol. 81: 13412-13423.

In one embodiment, a DNA reporter construct that indicates active viral replication and infection by EEV is created using the methods described in Ljungberg et al (2007) J. Virol. 81: 13412-13423.

In one embodiment, a viral replicon suitable for adaption into an at least one DNA reporter construct of the present invention is the Rubella virus replicon disclosed in Tzeng et al (2005) J. Clin Microbiol. 43: 879-885.

In one embodiment, a DNA reporter construct that indicates active viral replication and infection by Rubella virus is created using the methods described in Tzeng et al (2005) J. Clin Microbiol. 43: 879-885.

In one embodiment, a viral replicon suitable for adaption into an at least one DNA reporter construct of the present invention is SARS-CoV replicon disclosed in Ge et al (2008) Antiviral Research 80: 107-113.

In one embodiment, a DNA reporter construct that indicates active viral replication and infection by SARS-CoV is created using the methods described in Ge et al (2008) Antiviral Research 80: 107-113.

In one embodiment, a viral replicon suitable for adaption into an at least one DNA reporter construct of the present invention is the Hepatitis C virus replicon disclosed in Blight and Nogard, HCV Replicon Systems, Chapter 11.

In one embodiment, a DNA reporter construct that indicates active viral replication and infection by Hepatitis C is created using the methods described in Blight and Nogard, HCV Replicon Systems, Chapter 11.

Reporter Proteins: For the reporter, many fluorescent and bioluminescent reporter proteins are known and available for use and it is within the skill of the art to select a particular gene or operon encoding a reporter and to prepare the at least one DNA reporter construct of the invention. Fluorescent proteins (with their PDB databank designation) include, but are not limited to, GFP (green fluorescent protein), 1GFL; YFP (yellow fluorescent protein), 3DPW; BFP (blue fluorescent protein). 1BFP; Cerulean fluorescent protein 2WSO; Cyan fluorescent protein, 2WSN; RFP (red fluorescent protein from *Zooanthus* sp.), 2ICR; RFP (red fluorescent protein from *Entremacaea quadricolor*), 2PJB and the like. Another fluorescent protein for use in the invention is flavin mononucleotide (FMN)-binding fluorescent proteins (FbFPs). The excitation and emission wavelengths for these proteins are generally well known or can be readily determined.

Luminescent proteins suitable for use in the present invention include luciferase and aequorin.

The present invention also contemplates the use of reporter constructs that are capable of producing all the reagents or compounds necessary to emit a signal that can be detected. For example, a reporter construct may be designed that acts as a bio-sensor that generates the reporter protein and other proteins required to either cause the reporter protein to emit a signal, or enhance the signal from the reporter protein, or both. An example of such a reporter construct is the autonomous bioluminescent reporter encoding a bacterial luciferase systems encoded by luxCDABE, typically from a *Vibrio* species, described in Nivens et al. (2004) J. App. Microbiol. 96:33-46.

The present invention may also utilize reporters that generate other signals, such as, for example, a colorimetric signal, or a precipitate, or an enzyme that may be used in an enzyme-lined assay, and the like. Alternatively, the reporter may be an antigen.

In certain embodiments, the present invention provides a method for detecting the presence of more than one species and/or strain of virus in a sample obtained from a patient. In these embodiments, more than one DNA reporter constructs are employed, each of the DNA reporter constructs employed are specific for a single specific virus species or strain of virus, and each DNA reporter construct employs a different reporter, thereby enabling the method of the present invention to be "multiplexed" by virtue of each reporter emitting a signal that is readily discernable from the other reporter proteins. For example, a first reporter construct, comprising cis-acting replication elements to a first virus species or strain operably linked to a first reporter protein, may be used along with a second reporter construct, comprising cis-acting replication elements to a second virus species or strain operably linked to a second reporter protein in the method of the present invention. The first and second reporter constructs may be used with subsequent additional reporter constructs in the method of the present invention. Here, the array of the plurality of vertically aligned nanostructures are coated or covalently modified with a solution comprising a mixture of the first and subsequent DNA reporter constructs. The signals from the reporters constructs may then be detected using any instrument that is capable of detecting and discerning the signals from the reporter proteins.

Alternatively, the first reporter construct may be coated or covalently attached to a first area of the array of the plurality of vertically aligned nanostructures, and the second reporter construct may be coated or covalently attached to a second area of the array of the plurality of vertically aligned nanostructures. Subsequent reporter constructs are then applied to subsequent discrete areas of the array of the plurality of vertically aligned nanostructures. The reporter first and subsequent constructs may use the same reporter protein, or a different reporter protein. The signals from the first and subsequent reporter constructs may then be detected using any instrument that is capable of detecting and discerning the signals from the reporter proteins, both spatially, and via the spectral or physical properties of the first and subsequent reporter, if the first and subsequent reporter constructs utilize different reporter proteins.

Alternatively, the first and subsequent reporter constructs may be delivered as a single construct. The single construct may utilize a mechanism that allows multiple genes to be transcribed from a single mRNA message, such as, for example, via incorporating at least one internal ribosome entry site sequence into the reporter construct.

Apparatus capable of detecting and discerning the signals from the reporter proteins, both spatially, and via the spectral or physical properties of the first and subsequent reporter include, for example, an epifluorescent microscope, and the like. Selection of suitable apparatus may be easily achieved by one of skill in the art.

In one embodiment, the present invention provides a method for detecting the presence of more than one species and/or strain of virus in a sample obtained from a patient. In these embodiments, more than one DNA reporter constructs are employed, each of the DNA reporter constructs employed are specific for a single specific virus species or strain of virus, and each DNA reporter construct employs a reporter that contains a different targeting sequence, thereby enabling the method of the present invention to be "multiplexed" by virtue of each reporter emitting a signal that is readily discernable from the other reporter proteins by virtue of the localization of the signal within the cell. For example, a first reporter construct, comprising cis-acting replication elements to a first virus species or strain operably linked to a first reporter protein targeted to a first intracellular region, may be used along with a second reporter construct, comprising cis-acting replication elements to a second virus species or strain operably linked to a second reporter protein targeted to a second intracellular region in the method of the present invention. The first and second reporter constructs may be used with subsequent additional reporter constructs in the method of the present invention that are targeted to subsequent intracellular regions. Here, the array of the plurality of vertically aligned nanostructures are coated or covalently modified with a solution comprising a mixture of the first and subsequent DNA reporter constructs. The signals from the reporters constructs may then be detected using any instrument that is capable of detecting and discerning the signals from the reporter proteins.

Alternatively, the first reporter construct may be coated or covalently attached to a first area of the array of the plurality of vertically aligned nanostructures, and the second reporter construct may be coated or covalently attached to a second area of the array of the plurality of vertically aligned nanostructures. Subsequent reporter constructs are then applied to subsequent discrete areas of the array of the plurality of vertically aligned nanostructures. The reporter first and subsequent constructs may use the same reporter protein, or a different reporter protein.

The signals from the first and subsequent reporter constructs may then be detected using any instrument that is capable of detecting and discerning the signals from the reporter proteins, both spatially, and via the spectral or physical properties of the first and subsequent reporter, if the first and subsequent reporter constructs utilize different reporter proteins.

Alternatively, the first and subsequent reporter constructs may be delivered as a single construct. The single construct may utilize a mechanism that allows multiple genes to be transcribed from a single mRNA message, such as, for example, via incorporating at least one internal ribosome entry site sequence into the reporter construct.

Apparatus capable of detecting and discerning the signals from the reporter proteins, both spatially, and via the spectral or physical properties of the first and subsequent reporter include, for example, an epifluorescent microscope, and the like. Selection of suitable apparatus may be easily achieved by one of skill in the art.

Intracellular regions include, for example, the cytosol, the endoplasmic reticulum, the mitochondria, the nucleus, the lysosome, the secretory vesicles, to name a few.

In one embodiment, the first DNA reporter construct comprises cis-acting replication elements to a first virus species or strain operably linked to a first reporter protein, and the second or subsequent DNA reporter construct comprises a reporter protein, the expression of which is not viral-specific, but is employed to improve the signal to noise ratio of the signal of the viral-specific reporter protein signal.

For detecting the signal, if the reporter is a fluorophore, such as GFP, YFP, Venus, or other fluorescent reporter protein, a detection device provides fluorescent excitation and measures fluorescent emission. If the reporter is a luminescence gene or set of genes, such as the full LuxCD-ABE, which provides all the necessary elements for mammalian bioluminescence, then the device can simply measure bioluminescence (for example at 490 nm emission). Handheld devices are preferred for fieldable applications of the assay but laboratory spectrometers and the like can be used. Such devices can be CCD detectors to allow signal detection at the single cell level. In some cases, detection may be via a time-lapse fluorescent signal with monitoring the rate of signal gain (usually occurs in 20-60 min time frame after impaling the cells) relative to an unamplified control, which may be a reporter with a distinct spectral response discriminated from the virally-amplified signal, whereby the unamplified control mRNA is either not flanked by the viral UTR or the viral UTR is specifically altered to not be replicated by viral replication complexes by inclusion of non-sense sequences or other insertions or deletions that render the mRNA unrecognized by trans-acting viral replication factors.

The sensitivity of the method of the present invention may be altered and/or optimized by any suitable method that is readily selected by one of skill in the art. For example, the amount of DNA that is either coated or covalently bonded to the array of a plurality of vertically aligned high aspect ratio nanostructures may be altered or adjusted to provide the required sensitivity. By way of illustration, increasing the amount of DNA either coated or covalently bonded to the array of a plurality of vertically aligned high aspect ratio nanostructures will increase the number of copies of mRNA transcribed, and will produce a greater signal from the at least one reporter. Alternatively, the DNA that is either coated or covalently bonded to the array of a plurality of vertically aligned high aspect ratio nanostructures may be treated with an agent that stabilizes the DNA, thereby decreasing the degradation of the DNA.

In another example, the amount of reporter protein that is produced is increased by enhancing the rate and/or degree of transcription, by performing an initial transcription step at 37° C., followed by a viral replication step at a temperature optimized for the virus that is to be detected, followed by a viral translation step at a temperature optimized for the virus that is to be detected. By way of illustration, many mosquito-borne viruses replicate at 25° C. In these instances, sensitivity of the present invention may be increased by performing the viral replication and/or the viral translation steps at temperatures at or close to the temperature the virus would perform them in nature.

In another example, the amount of reporter protein that is produced is increased by enhancing the rate and/or degree of transcription, by performing the method of the present invention at, or near 37° C.

In another example, the sample may be treated with an agent that enhances expression. In one embodiment, the agent that enhances expression is a histone deacetylase inhibitor. In one embodiment, the histone deacetylase inhibitor is sodium butyrate.

In another example, the sensitivity of the method of the present invention is enhanced by enriching the sample for a specific subset of cells. In one embodiment, the specific subset of cells are the cells that are likely or known to be infected by the virus that the method of the present invention is being used to detect.

In another example, the sensitivity of the method of the present invention is enhanced by obtaining the sample from the site of viral infection.

In one embodiment, the signal to noise ratio of the method of the present invention is improved via the use of at least one DNA reporter construct that launches the mRNA replicon from a promoter that contains a cis-acting repressor site. In one embodiment, the at least one reporter contains a nucleotide sequence encoding a UTR-flanked reporter and nucleotide sequence encoding cytomegalovirus IE2 protein with a cis-acting repressor site in the cytomegalovirus IE2 promotor. Impalefection results in the production of both the UTR-flanked reporter and IE2 protein in all cells transfected. The IE2 binds to the cis-acting repressor site and suppresses further transcription of the UTR flanked replicon mRNA. Signal from the reporter protein will only be detectable if viral-mediated replication produces more of the UTR-flanked mRNA.

The present invention provides a kit with cell-penetrable, nanostructured spikes formed into a vertically aligned carbon nanofiber array which can optionally be spatially indexed and with a reporter DNA construct adhered to or carried on the spikes. The reporter DNA construct encodes mRNA featuring cis-acting replication elements operably linked to a reporter gene or operon and comprises the 5' and 3' RNA viral untranslated regions and any additional adjacent sequences necessary for viral replication flanking said reporter operon. The RNA viral elements are from a human or animal pathogenic RNA virus as described herein, and includes such viruses as Hanta, Dengue, Ebola, Marburg, Lassa, Hepatitis A, Hepatitis C, Yellow Fever or West Nile virus or other human encephalitis virus, and the animal viruses foot and mouth disease virus, Rift Valley fever virus, common swine fever virus, or Japanese encephalitis virus. The reporter gene or operon is as described hereinabove. Similar constructs and methods for detection of plant viral infections are also possible, but use DNA launched reporter genes expressible in plants using constitutively expressed promoters functional in plants.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

EXAMPLE 1

Dengue Diagnostic Constructs

A Dengue virus (DenV) reporter system for deployment in suspect infected tissue for rapid determination of active Dengue viral infection is generated as per Leardkamolkarn et al (2012 Viral Res. 163: 552-562 with viral protein NS5 deleted to eliminate production of NS5 replicase from the DNA-launched reporter itself; thereby rendering the mRNA amplified only in the presence of active Dengue infection which supplies the requisite NS5 for amplification. The DNA launched reporter construct is delivered using the impalefection technology disclosed in McKnight 2004, 2005 into DenV-infected and uninfected-control cells representative of viral lesions (HDF, human dermal fibroblasts) and isolated leukocytes (J774a.1, macrophages) both of which are known to serve as replication hosts for DenV in vivo.

Co-delivery of a non-amplified reporter protein (CMVie-dsRED) is used as an internal control that is not amplified by active viral replication. This may either be in the form of a construct that encodes an mRNA completely lacking the viral flanking UTR sequences, or the viral flanking sequences may be modified via insertion/deletions/substitutions rendering it unreplicated by active viral infection. Positive control DNA-launched replicons may also be used in some delivery assays that encode for both a unique spectral reporter protein (such as CFP) as well as all the viral transacting factors required for replication of the UTR-flanked RNA. mRNA from such DNA-launched positive controls will thereby be amplified in cells without active viral infection due to their self-production of all required trans-acting replication factors. Such positive controls cannot be used in cells being assayed for viral infection, due to the interference caused by the self-generation of viral trans-acting replication factors. Positive controls are performed in separate cells or tissue such that the viral reporter (GFP) is only amplified by the presence of actual viral replication factors due to actual viral infection. Time-lapse fluorescence microscopy is used to track the fluorescent signal trajectories of both the virally-sensitive GFP reporter, the virally-insensitive dsRED negative control, and of the positive control (CFP) in separate delivery assays.

Previous work has demonstrated that impalefection provides extremely rapid transgene expression, with the pd2eYFP-N1 and pVenus-N1 reporters providing measurable signal within cells within 27 minutes after impalefection-mediated nuclear gene delivery. GFP-based reporter fusion proteins (GFP-zonula occludens 2) provide less rapid signal (detection onset at approximately 50 min) either due to longer maturation times required for GFP fluorescence or due to differences imparted by expression and translation of fusion proteins. With the addition of the viral amplification of the intermediate GFP-mRNA, the onset and rate of increase of the DenV GFP-reporter signal is expected to provide a rapid and potentially quantitative measure of viral replication activity within the tissue. If quantitation is not achieved through the GFP signal alone, the assay design can incorporate the potential of using the control dsRED signal for two-color ratiometric comparison of the virally-amplified GFP vs. the unamplified dsRED (or other discrete spectral reporter) to provide correction for effects associated with the stoichiometry of DNA delivery (variable copy number) and target specific variations in expression dynamics.

DENV Serotype-2 Vaccine strain can be propagated in *Aedes albopictus* C6/36 cells. Standard viral characterization and use protocols are employed. Virus titers are measured by plaque assay with Baby Hamster Kidney (BHK) cells. Direct and antibody-dependent enhanced infections using murine 2H2 and 4G2 antibodies are conducted using an established protocol with minor modifications [Chan 2012]. Briefly, DENV2 is incubated in DMEM containing 2% FBS with or without enhancing titers of 2H2 (20 ng for MOI 1 and 200 ng for MOI 10) or 4G2 antibodies (approximately 20 ng for both MOI 1 and 10) in a total volume of 250 μl for 30 min at 37° C. Murine lymphocyte cells (J774a.1) and dermal fibroblasts (HDF) are propagated in 25-cm$^2$ flasks. After incubation with various titers of viral challenge for 1.5 h at 37° C., cells are washed with PBS and media renewed and incubated for various lengths of time (4 hrs, 12 hrs, 24 hrs, 48 hrs) before harvesting cells for viral diagnostics (or supernatant or plaque assay).

EXAMPLE 2

Leukocyte Diagnostic System

The reporter assay is configured from a clinical, laboratory environment to one that can be conducted in remote, field sites without clinical infrastructure. To do this, the isolation and impalefection of peripheral blood mononucleated cells (PBMCs) from finger pricks can be assayed. Currently, impalefection is implemented using both intact tissue and cell cultures comprising suspensions of cells. For the latter, the cell suspension is centrifuged into a pellet against which DNA-modified nanostructure arrays are pressed. After a gentle rinse, impaled cells remain resident upon the small 2.2 mm square impalefection device, and it is upon this device that transgene expression is rapidly observed. The requirements of centrifugation can be eliminated and provide the ability to directly impale isolated leukocytes from finger pricks. Further, small, battery-powered fieldable units capable of measuring reporter response dynamics can be used as in Example 1.

Pall Leukosorb size exclusion media is used as a highly-fieldable means of isolating PBMCs. This media is essentially a porous filter paper, where size exclusion enables gravimetric flowthrough of serum, platelets, and RBCs. Larger PBMCs are collected on the surface of the hydrophilic Leukosorb filter with published capture efficiencies of approximately 40-50%. A typical finger prick yields approximately 0.05 mL of whole blood and contains upwards to 300,000 leukocytes. Impalement of leukocytes on the surface of Leukosorb filters provides impalement of approximately 10,000 cells and efficient delivery of the DenV-reporter construct. Upon impalement, fieldable readout of the diagnostic is achieved using a battery powered unit comprised of laser diode excitation, channel-photomultiplier detection, and associated spectral and spatial optics.

REFERENCES

Alcaraz-Estrada S L, Yocupicio-Monroy M, del Angel R M (2010). Insights into dengue virus genome replication. Future Virol 5(5), 575-592.

Chan Y K, Huang I-C, Farzan M (2012). IFITM Proteins Restrict Antibody-Dependent Enhancement of Dengue Virus Infection. PLoS ONE 7(3): e34508. doi:10.1371/journal.pone.0034508

Dominguez C, Boelens R and A. M. J. J. Bonvin, "HADDOCK: a protein-protein docking approach based on biochemical and/or biophysical information.", J. Am. Chem. Soc. 125, 1731-1737, 2003.

Manzano M, Reichert E D, Polo S, Falgout B, Kasprzak W, Shapiro B A, Padmanabhan R (2011). Identification of cis-acting elements in the 3'-untranslated region of the dengue virus type 2 RNA that modulate translation and replication. J. Bio. Chem 286(25), 22521-22534.

Gebhard L G, Filomatori C V, Gamarnik A V (2011). Functional RNA elements in the Dengue Virus Genome. Viruses 3, 1739-1756.

Kalorama Information (2012). Worldwide market for IVD tests 8th edition.

Mann, D. G. J., McKnight T E, McPherson J T, Hoyt P R, Melechko A V, Simpson M L, Sayler G S. Inducible RNA Interference-Mediated Gene Silencing Using Nanostructured Gene Delivery Arrays. ACS Nano 2(1): 69-76, 2008.

McKnight T E, Melechko A V, Griffin G D, Guillorn M A, Simpson M L. Synthetic nanoscale elements for delivery of materials into viable cells. Methods Mol Biol 303: 191-208, 2005.

McKnight T E, Melechko A V, Hensley D K, Griffin G D, Mann D, Simpson M L, Tracking Gene Expression after DNA Delivery Using Spatially Indexed Nanofiber Arrays, NanoLetters 4(7): 1213-1219. 2004.

Shapiro B A, Bengali D, Kasprzak W and J. C. Wu, "RNA folding pathway functional intermediates: Their prediction and analysis", J. Mol. Biol. 312, 27-44, 2001.

Sharma S, Ding F, and Dokholyan N V, "iFoldRNA: Three-dimensional RNA structure prediction and folding" Bioinformatics, 24: 1951-1952, 2008.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. A method for rapid diagnosis of infection by a RNA virus in a sample which comprises (a) adsorbing either (i) a sample of blood onto a porous filter to entrap leukocytes but permit gravimetric flow through of platelets and red blood cells, thereby obtaining a sample of leukocytes, (ii) a tissue sample onto a filter or other surface, (iii) a biological fluid sample onto a filter or other surface, or (iv) a sample of leukocytes onto a filter or other surface;

(b) impaling cells in said sample on the filter or surface onto an array of a plurality of vertically aligned nanostructures carrying at least one DNA reporter construct thereon, wherein the at least one DNA reporter construct encodes an mRNA viral replicon, wherein said viral replicon comprises cis-acting RNA viral replication elements and any other adjacent regions necessary for viral replication of said RNA virus flanking and operably linked to a reporter gene or operon, wherein said viral replicon lacks a nucleic acid encoding at least one factor required for viral replication and provided in trans by cells infected by said RNA virus, and wherein the viral replicon is amplified in cells infected by said RNA virus but not in cells not infected by said virus; and (c) detecting expression of said reporter gene or operon, wherein the expression of said reporter gene is indicative of a RNA virus infection.

2. The method of claim 1, wherein expression of said reporter gene or operon occurs by virally-mediated replication and amplification of RNA encoding said reporter gene or operon.

3. The method of claim 1, wherein detecting expression is by detecting amplification of a signal from said reporter gene or operon when virally-infected cells are present.

4. The method of claim 3, wherein a non-amplifiable reporter DNA construct with a distinct spectral response is co-delivered with said at least one DNA reporter construct to allow ratiometric comparison of amplified and unamplified signals to account for cell- or tissue-specific expression dynamics and variation in stoichiometries of DNA delivered to each cell.

5. The method of claim 4, wherein said ratiometric comparison is conducted temporally.

6. The method of claim 1, wherein said sample is washed with buffer prior to step (b).

7. The method of claim 1, wherein said blood sample is from about 10 to about 100 microliters.

8. The method of claim 1 wherein said porous filter is Leukosorb.

9. The method of claim 1, wherein said sample of leuokocytes is prepared by a conventional leukocyte enrichment protocol.

10. The method of claim 1, wherein said array of a plurality of vertically aligned nanostructures comprise nanostructures selected from the group consisting of nanospikes, nanotubes, micro-machined needles and microneedles.

11. The method of claim 10, wherein said array is spatially indexed.

12. The method of claim 1, wherein said cis-acting RNA viral replication elements are selected from a human or animal pathogenic RNA virus.

13. The method of claim 12, wherein said human pathogenic RNA virus is a Hanta, Dengue, Ebola, Marburg, Lassa, Hepatitis A, Hepatitis C, Yellow Fever or West Nile virus or other human encephalitis virus.

14. The method of claim 12, wherein said animal pathogenic RNA virus is foot and mouth disease virus, Rift Valley fever virus, common swine fever virus, or Japanese encephalitis virus.

15. The method of claim 1, wherein said cis-acting replication elements operably linked to a reporter gene or operon comprise 5' and 3' RNA virus untranslated regions.

16. The method of claim 1, wherein said reporter gene or operon encodes a fluorescent reporter protein or protein complex, or a bioluminescent reporter protein or protein complex.

17. The method of claim 16, wherein said fluorescent reporter protein is selected from the group consisting of GFP, YFP, BFP or RFP.

18. The method of claim 16, wherein said bioluminescent reporter protein complex is LuxCDABE.

19. The method of claim 1, wherein expression is detected by fluorescence or luminescence.

20. The method of claim 19, wherein fluorescence is detected with a battery-powered unit providing laser diode excitation and channel-photomultiplier detection.

21. The method of claim 19, wherein fluorescence is detected by microscopy.

22. The method of claim 1, wherein the at least one viral replication factor is a viral replicase specific to said RNA virus.

23. The method of claim 22, wherein the replicase is an NS5 replicase.

24. The method of claim 22, wherein the virus is a Dengue virus.

* * * * *